(12) United States Patent
Owen et al.

(10) Patent No.: US 9,778,215 B2
(45) Date of Patent: Oct. 3, 2017

(54) AUTOMATED MINERAL CLASSIFICATION

(71) Applicant: FEI Company, Hillsboro, OR (US)

(72) Inventors: Michael James Owen, Geebung (AU); Michael Buhot, Brisbane (AU)

(73) Assignee: FEI Company, Hillsboro, OR (US)

( * ) Notice: Subject to any disclaimer, the term of this patent is extended or adjusted under 35 U.S.C. 154(b) by 65 days.

(21) Appl. No.: 13/662,072

(22) Filed: Oct. 26, 2012

(65) Prior Publication Data
US 2014/0117231 A1    May 1, 2014

(51) Int. Cl.
*G01N 23/225* (2006.01)
*H01J 37/28* (2006.01)
*H01J 37/256* (2006.01)

(52) U.S. Cl.
CPC ........ *G01N 23/2252* (2013.01); *H01J 37/256* (2013.01); *H01J 37/28* (2013.01); *G01N 2223/418* (2013.01); *H01J 2237/2442* (2013.01); *H01J 2237/24425* (2013.01); *H01J 2237/2804* (2013.01); *H01J 2237/2807* (2013.01)

(58) Field of Classification Search
CPC .............. G01N 23/203; G01N 23/225; G01N 23/2252; H01J 223/2442; H01J 223/24425
See application file for complete search history.

(56) References Cited

U.S. PATENT DOCUMENTS

| | | |
|---|---|---|
| 4,037,101 A | 7/1977 | Okumura et al. |
| 4,136,429 A | 1/1979 | Brandes |
| 4,242,586 A | 12/1980 | Warble |
| 4,435,507 A | 3/1984 | Stenkvist |
| 4,476,386 A * | 10/1984 | Reid ............... G01N 23/22  250/307 |
| 4,587,424 A | 5/1986 | Grau |
| 4,592,082 A | 5/1986 | Pawloski |
| 4,807,148 A | 2/1989 | Lacey |
| 4,834,943 A | 5/1989 | Yoshiyama |
| 4,839,516 A | 6/1989 | Freeman et al. |

(Continued)

FOREIGN PATENT DOCUMENTS

| | | |
|---|---|---|
| AU | 2012201146 | 10/2012 |
| CN | 100498309 | 6/2009 |

(Continued)

OTHER PUBLICATIONS

Pye, "Rapid Estimation of Porosity and Mineral Abundance in Backscattered Electron Images Using a Simple SEM image analyzer", Geological Magazine, vol. 121, No. 2, 1984.*

(Continued)

*Primary Examiner* — Wyatt Stoffa
*Assistant Examiner* — James Choi
(74) *Attorney, Agent, or Firm* — Scheinberg & Associates, P.C.; Michael O. Scheinberg; John E. Hillert (57) ABSTRACT

The present invention discloses a combination of two existing approaches for mineral analysis and makes use of the Similarity Metric Invention, that allows mineral definitions to be described in theoretical compositional terms, meaning that users are not required to find examples of each mineral, or adjust rules. This system allows untrained operators to use it, as opposed to previous systems, which required extensive training and expertise.

19 Claims, 4 Drawing Sheets

(56) References Cited

U.S. PATENT DOCUMENTS

| | | | |
|---|---|---|---|
| 5,084,618 A | 1/1992 | Ito | |
| 5,555,198 A | 9/1996 | Asano | |
| 5,557,104 A * | 9/1996 | Field | G01N 23/203 250/306 |
| 5,569,925 A * | 10/1996 | Quinn et al. | 250/370.06 |
| RE35,514 E | 5/1997 | Albrecht et al. | |
| 5,741,707 A | 4/1998 | Herron et al. | |
| 5,798,525 A | 8/1998 | Benizri-Carl et al. | |
| 5,866,903 A | 2/1999 | Morita et al. | |
| 5,906,919 A | 5/1999 | Garini et al. | |
| 5,991,028 A | 11/1999 | Cabib et al. | |
| 6,018,587 A | 1/2000 | Cabib | |
| 6,066,459 A | 5/2000 | Garini et al. | |
| 6,072,178 A | 6/2000 | Mizuno | |
| 6,093,930 A | 7/2000 | Boyette, Jr. et al. | |
| 6,122,343 A | 9/2000 | Pidcock | |
| 6,140,643 A * | 10/2000 | Brown | G01N 23/063 378/48 |
| 6,282,301 B1 | 8/2001 | Haskett | |
| 6,341,257 B1 | 1/2002 | Haaland | |
| 6,377,652 B1 | 4/2002 | Sturm | |
| 6,466,929 B1 | 10/2002 | Brown et al. | |
| 6,470,335 B1 | 10/2002 | Marusak | |
| 6,584,413 B1 | 6/2003 | Keenan et al. | |
| 6,658,143 B2 | 12/2003 | Hansen et al. | |
| 6,674,894 B1 | 1/2004 | Parker et al. | |
| 6,687,620 B1 | 2/2004 | Haaland et al. | |
| 6,711,503 B2 | 3/2004 | Haaland | |
| 6,723,871 B2 | 4/2004 | Tada et al. | |
| 6,724,940 B1 | 4/2004 | Qian et al. | |
| 6,765,205 B2 | 7/2004 | Ochiai et al. | |
| 6,835,931 B2 * | 12/2004 | Wright | G01N 23/203 250/307 |
| 6,842,702 B2 | 1/2005 | Haaland et al. | |
| 6,888,920 B2 | 5/2005 | Blank et al. | |
| 6,977,723 B2 | 12/2005 | Lemmo et al. | |
| 6,993,170 B2 | 1/2006 | Johnson et al. | |
| 6,996,492 B1 * | 2/2006 | Testoni | 702/134 |
| 7,053,365 B2 | 5/2006 | Shimomura | |
| 7,061,605 B2 | 6/2006 | Lemmo et al. | |
| 7,108,970 B2 | 9/2006 | Levinson | |
| 7,132,652 B1 | 11/2006 | Testoni | |
| 7,139,415 B2 | 11/2006 | Finkbeiner | |
| 7,161,672 B2 | 1/2007 | Gornushkin et al. | |
| 7,243,030 B2 | 7/2007 | Reeve et al. | |
| 7,244,948 B1 | 7/2007 | Gentile et al. | |
| 7,400,770 B2 | 7/2008 | Keaton et al. | |
| 7,436,510 B2 | 10/2008 | Grun et al. | |
| 7,490,009 B2 | 2/2009 | Gottlieb et al. | |
| 7,595,489 B2 | 9/2009 | Statham | |
| 7,711,661 B2 | 5/2010 | Gentile et al. | |
| 7,790,465 B2 | 9/2010 | Otvos | |
| 7,804,059 B2 | 9/2010 | Harrison | |
| 7,877,340 B2 | 1/2011 | Gentile et al. | |
| 7,930,106 B2 | 4/2011 | Carrick | |
| 7,979,217 B2 | 7/2011 | Gottlieb et al. | |
| 8,060,173 B2 | 11/2011 | Goode, Jr. et al. | |
| 8,093,556 B2 * | 1/2012 | Zeile | G01N 23/2251 250/306 |
| 8,119,991 B2 | 2/2012 | Harrison | |
| 9,048,067 B2 * | 6/2015 | Owen | G01N 23/2252 |
| 2002/0169589 A1 | 11/2002 | Banki et al. | |
| 2004/0011958 A1 | 1/2004 | Wright et al. | |
| 2004/0027350 A1 | 2/2004 | Kincaid et al. | |
| 2004/0057040 A1 | 3/2004 | Beckenkamp et al. | |
| 2004/0099805 A1 | 5/2004 | Ochiai et al. | |
| 2004/0147830 A1 | 7/2004 | Parker et al. | |
| 2005/0037515 A1 | 2/2005 | Nicholson et al. | |
| 2005/0060868 A1 | 3/2005 | McMurtry | |
| 2005/0165290 A1 | 7/2005 | Kotsianti et al. | |
| 2006/0051251 A1 | 3/2006 | Desrosiers et al. | |
| 2006/0291619 A1 * | 12/2006 | Statham | 378/45 |
| 2007/0181793 A1 | 8/2007 | Harrison | |
| 2007/0278415 A1 | 12/2007 | Gentile et al. | |
| 2007/0279629 A1 | 12/2007 | Grun et al. | |
| 2008/0007379 A1 * | 1/2008 | Inagaki | H01F 38/12 336/90 |
| 2008/0137082 A1 | 6/2008 | Grun et al. | |
| 2008/0250881 A1 | 10/2008 | Dona | |
| 2010/0060893 A1 | 3/2010 | Norton et al. | |
| 2011/0144922 A1 | 6/2011 | Corbett et al. | |
| 2011/0301869 A1 * | 12/2011 | Gottlieb | G01N 23/2206 702/32 |
| 2013/0015351 A1 | 1/2013 | Kooijman et al. | |
| 2013/0054153 A1 * | 2/2013 | Motl | H01J 37/222 702/28 |
| 2013/0134307 A1 | 5/2013 | Routh, Jr. | |
| 2016/0116425 A1 * | 4/2016 | Sinha | G01N 23/2252 250/307 |
| 2016/0245762 A1 * | 8/2016 | Owen | G01N 23/2252 |

FOREIGN PATENT DOCUMENTS

| | | |
|---|---|---|
| GB | 2223842 A | 4/1990 |
| JP | S57500796 A | 5/1982 |
| JP | H03073833 | 3/1991 |
| JP | 05087707 | 4/1993 |
| JP | 08015185 | 1/1996 |
| JP | 10312763 | 11/1998 |
| JP | H11174005 | 7/1999 |
| JP | 2000249668 | 9/2000 |
| JP | 2001006597 | 1/2001 |
| JP | 2001066269 | 3/2001 |
| JP | 2002189005 | 7/2002 |
| JP | 2005274352 | 10/2005 |
| JP | 2006113063 A | 4/2006 |
| JP | 2007003532 A | 1/2007 |
| JP | 2011113640 | 6/2011 |
| RU | 2054660 | 2/1996 |
| WO | 9905503 | 2/1999 |
| WO | 2008013597 | 1/2008 |
| WO | 2009100404 | 8/2009 |

OTHER PUBLICATIONS

Sutherland et al., "Application of Automated Quantitative Mineralogy in Mineral Processing", Minerals Engineering, vol. 4, Nos. 7-11, pp. 753-762, 1991.*

Ayling et al., "QEMSCAN (Quantitative Evaluation of Minerals by Scanning Electron Microscopy): Capability and Application to Fracture Characterization in Geothermal Systems", Proceedings, Thirty-Seventh Workshop on Geothermal Reservoir Engineering, Stanford University, Stanford, California, Jan. 30-Feb. 1, 2012.*

Sylvester, "Use of the Mineral Liberation Analyzer (MLA) for mineralogical studies of sediments and sedimentary rocks", Jan. 2012.*

Ashton, Edward A., "Multialgorithm solution for automated multispectral target detection," Opt. Eng., Apr. 1999, pp. 717-724, vol. 38, No. 4.

Benz, Ursula C., et al., "Multi-resolution, object-oriented fuzzy analysis of remote sensing data for GIS-ready information," ISPRS Journal of Photogrammetry & Remote Sensing, 2004, pp. 239-258, vol. 58.

Creelman, Robert A., et al., "A scanning electron microscope method for automated, quantitative analysis of mineral matter in coal," International Journal of Coal Geology, 1996, pp. 249-269, vol. 30.

Unknown, "Energy-dispersive X-ray spectroscopy," Wikepedia, http://en.wikipedia.org/wiki/Engergy_Dispersive_Spectroscopy, obtained Jul. 29, 2013, 3 pages.

Fandrich, Rolf, et al., "Modern SEM-based mineral liberation analysis," Int. J. Miner. Process., 2007, pp. 310-320, vol. 84.

Figueroa, German, et al., "Advanced Discrimination of Hematite and Magnetite by Automated Mineralogy," 10th ICAM, Aug. 1-5, 2011, pp. 197-204.

Furse, J.E., "Kinematic design of fine mechanisms in instruments," J. Phys. E: Sci. Instrum., 1981, pp. 264-272, vol. 14.

Ghassemian, Hassan, et al., "Object-Oriented Feature Extraction Method for Image Data Compaction," IEEE Control Systems Magazine, Jun. 1998, pp. 42-48.

(56) References Cited

OTHER PUBLICATIONS

Gottlieb, P., et al., "The Automatic Identification and Quantification of Silver Minerals," XVIII International Mineral Processing Congress, May 23-28, 1993, pp. 475-481.

Gottlieb, P. et al., "Using Quantitative Electron Microscopy for Process Mineralogy Applications," JOM, Apr. 2000, pp. 24-25.

Hale, Layton C., et al., "Optimal design techniques for kinematic couplings," Journal of the International Societies for Precision Engineering and Nanotechnology, 2001, pp. 114-127, vol. 25.

Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.

Jana, Dipayan, "Sample Preparation Techniques in Petrographic Examinations of Construction Materials: A State-of the-Art Review," Proceedings of the twenty-eighth Conference on Cement Microscopy, Apr. 30-May 4, 2006, 48 pages.

Lapicki, Adam, et al., "Kinematic sample mounting system for accurate positioning of transferrable samples," J. Vac. Sci. Technol. A, Sep./Oct. 2000, pp. 2603-2605, vol. 18 No. 5.

Meyer, K., et al., "Qualitative and quantitative mixture analysis by library search: infrared analysis of mixtures of carbohydrates," Analytica Chimica Acta, 1993, pp. 161-171, vol. 281.

Miller, Jeff, "Jeff's (Fairly Comprehensive) Raith Usage Notes," Marcus Group, Harvard University, Unknown date Version 20040929.1, 12 pages.

Newbury, Dale E., "Chemical compositional mapping by microbeam analysis at the micrometer scale and finer," Microelectronics Journal, 1997. pp. 489-508, vol. 28.

Newbury, Dale "Pushing the Envelope with SEM/SDD-EDS Mapping: X-ray Spectrum Image Mapping in 30 Seconds or Less, But What are the Real Limits?" Proc. of SPIE, 2010, 9 pages, vol. 7729.

Oversluizen, Tom, et al., "Kinematic mounting systems for National Synchrotron Light Source beamlines and experiments," Rev. Sci. Instrum., Jan. 1992, pp. 1285-1288, vol. 63 No. 1.

Pirrie, Duncan, et al., "Rapid quantitative mineral and phase analysis using automated scanning electron microscopy (QemSCAN); potential applications in forensic geoscience," Forensic Geoscience: Principles, Techniques and Applications, 2004, pp. 123-136.

Pye, Kenneth, et al., "Forensic Geoscience: Principles, Techniques and Applications," The Geological Society, Mar. 3 & 4, 2003, 55 pages.

Pye, Kenneth, et al., "Forensic Geoscience: Principles, Techniques and Applications," The Geological Society, 2004, 25 pages.

Slocum, A. H., "Kinematic couplings for precision fixturing—Part I: Formulation of design parameters," Precision Engineering, Apr. 1988, pp. 85-92, vol. 10 No. 2.

Slocum, A. H., et al., "Kinematic couplings for precision fixturing—Part 2: Experimental determination of repeatability and stiffness," Precision Engineering, Jul. 1988, pp. 115-122, vol. 10 No. 3.

Slocum, Alexander H., "Design of three-groove kinematic couplings," Precision Engineering, Apr. 1992, pp. 67-77, vol. 14, No. 2.

Slocum, Alexander, "Kinematic couplings: a review of design principles and applications," International Journal of Machine Tools & Manufacture, 2010, pp. 310-327, vol. 50.

Sutherland, D. N., et al., "Application of Automated Quantitative Mineralogy in Mineral Processing," Minerals Engineering, 1991, pp. 753-762, vol. 4 No. 7-11.

Sutherland, D. N., "Image Analysis for Off-Line Characterisation of Mineral Particles and Prediction of Processing Properties," Part. Part. Syst. Charact., 1993, pp. 271-274, vol. 10.

Unknown, "Raith e_LINE User Guide," online, Nov. 2009,18 pages.

Van Hoek, Corrie J.G., et al., "A SEM-EDS Study of Cultural Heritage Objects with Interpretation of Constituents and Their Distribution Using PARC Data Analysis," Microsc. Microanal. 2011, pp. 656-660, vol. 17.

Zelenika, S., et al., "Kinematic Couplings for Synchrotron Radiation Instrumentation," 2nd International Workshop on Mechanical Engineering Design of Synchrotron Radiation Equipment and Instrumentation, Sep. 5-6, 2002, 9 pages.

\* cited by examiner

AUTOMATED MINERAL CLASSIFICATION

TECHNICAL FIELD OF THE INVENTION

The present invention relates generally to methods and structures for identifying minerals using charged particle beam systems with x-ray spectroscopy.

BACKGROUND OF THE INVENTION

A scanning electron microscope (SEM) is a type of electron microscope that images a sample by scanning it with a focused beam of electrons in a predetermined pattern. The electrons interact with the atoms that make up the sample producing signals that provide information about the sample's surface topography, composition, and other properties.

The types of signals produced by an SEM include secondary electrons, back-scattered electrons (BSE), characteristic X-rays, light (cathodoluminescence), specimen current and transmitted electrons. The signals result from interactions of the electron beam with atoms at or near the surface of the sample. In one common detection mode, secondary electron imaging (SEI), the SEM can produce very high-resolution images of a sample surface, revealing details less than 1 nm in size. Due to the very narrow electron beam, SEM micrographs have a large depth of field yielding a characteristic three-dimensional appearance useful for understanding the surface structure of a sample.

Scanning electron microscopes are used in mineral analysis systems, such as the Qemscan® and MLA® available from FEI Company, Hillsboro, Oreg., have been used for many years to analyze mineral samples. To determine the type and relative quantity of minerals present in a mine, a sample in the form of small granules, is fixed in epoxy in a mold and the mold is placed in a vacuum chamber. An electron beam is directed toward a sample and, in a process called x-ray spectroscopy, the energies of x-rays coming from the sample in response to the electron beam are measured and plotted in a histogram to form a spectrum. The measured spectrum can be compared to the known spectra of various elements to determine which elements and minerals are present. One type of x-ray spectroscopy is "energy dispersive x-ray spectroscopy" or "EDS." Another type is "wavelength dispersive spectroscopy," or "WDS."

To stimulate the emission of characteristic X-rays from a specimen, a high-energy beam of charged particles such as electrons or protons, or a beam of X-rays, is focused into the sample being studied. At rest, an atom within the sample contains ground state (or unexcited) electrons in discrete energy levels or electron shells bound to the nucleus. The incident beam may excite an electron in an inner shell, ejecting it from the shell while creating an electron hole where the electron was. An electron from an outer, higher-energy shell then fills the hole, and the difference in energy between the higher-energy shell and the lower energy shell may be released in the form of an X-ray. The unique atomic structure of each element allows x-rays that are characteristic of an element's atomic structure to be uniquely identified from one another. The number and energy of the X-rays emitted from a specimen can be measured by an x-ray spectrometer, such as an EDS or a wavelength dispersive spectrometer, to determine the elemental composition of the specimen to be measured.

Back-scattered electrons (BSE) are electrons from the primary electron beam that are reflected from the sample by elastic or inelastic scattering. BSE are often used in analytical SEM along with the spectra made from the characteristic X-rays, because the intensity of the BSE signal is strongly related to the atomic number (Z) of the specimen. BSE images can provide information about the distribution of different elements in the sample.

BSE signals are typically acquired at a rate of microseconds per pixel. EDS systems have a longer acquisition time, typically requiring on the order of several seconds per pixel to produce a spectrum having sufficient resolution to uniquely identify a mineral. The longer time required to collect an x-ray spectrum to uniquely identify a mineral substantially limits the number of pixels that can be measured. EDS systems are also typically insensitive to light atoms. Because of the advantages of both EDS detectors and BSE detectors, it is sometimes useful to use both BSE and x-ray spectra to accurately identify minerals, which requires more time and becomes a difficult problem to solve with a commercially viable approach.

The Qemscan® and MLA® systems comprise an SEM, one or more EDS detectors, and software for controlling data acquisition. These systems identify and quantify elements represented within an acquired spectrum, and then match this elemental data against a list of mineral definitions with fixed elemental ranges.

Some mineral classification systems compare the acquired spectrum of an unknown mineral to a library of known mineral spectrums, and then identify the sample based on which known spectrum that is most similar to the sample's spectrum. There are various ways to compare two spectrums directly. For example, one can take the sum of the differences between the two spectrums at different energy channels as a "distance." The MLA, uses a chi-squared statistical test to compare the value at each energy channel of the measured spectrum to the value at the corresponding channel of the known mineral spectrum. The MLA assigns the unknown spectrum to the element having the "best match" to the spectrum, as long as a minimum similarity is met.

QEMSCAN, on the other hand, uses a system of rules or criteria that, if met, classify the spectrum. This is typically applied in a "first match" manner, that is, the spectrum is compared sequentially to the criteria for each possible mineral, and when the spectra meets a criteria, the system assigns that element to the spectrum.

Existing systems require expert users to spend time i) locating and collecting examples of minerals to use as standards to compare against the unknown spectrum (MLA) or ii) formulating a list of rules that are applied sequentially to identify a mineral (QEMSCAN). These requirements have made it difficult to make an automated mineral identification system or even a system that can be used by relatively unskilled operators.

SUMMARY OF THE INVENTION

An object of the invention is to efficiently classify mineral samples analyzed by x-ray spectroscopy.

The invention combines a rules-based approach with a similarity metric approach. The combination provides synergistic benefits beyond those that would be expected from the approach applied individually. Embodiments of the invention simplify the mineral identification process so that it can be automated.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION

Embodiments of the present invention are directed towards a method for efficiently and easily classifying minerals based on an x-ray spectrum.

This invention describes a robust method that can be automated to identify a mineral from SEM-EDS data without human intervention. Combining a rules-based approach with a best match approach provides the unexpected benefit of decreasing the analysis time and increasing the robustness of the analysis. In some embodiments, a first match, rules-based approach is used to eliminate data points that are not of interest, such as data points that represent the resin between mineral samples or data points that represent a crack in a sample, which provides unreliable readings. A "data point" corresponds to a position on the sample, either a single dwell point or multiple, grouped dwell points, and can include one or more types of information, such as an x-ray spectrum and back scattered electron information, from that position on the sample. The rules applied for such preliminary screening are typically different from the rules typically applied when the rules-based, first match, system is used alone. The different rules provide benefits that would not accrue from merely applying prior art systems in sequence.

One embodiment uses in the "Best Match" analysis, the similarity metric described in 'Mineral Identification Using Mineral Definitions Including Variability' as described in U.S. patent application Ser. No. 13/661,774, filed Oct. 26, 2012, where is hereby incorporated by reference. This analysis, when used with the present invention, eliminates the need for expert users to locate and collect examples of minerals to compare measured data against for determining a similarity metric or formulating a list of rules that are applied sequentially to identify a mineral. This system allows untrained operators to use it, as opposed to previous systems that required extensive training and expertise.

Figure 1:
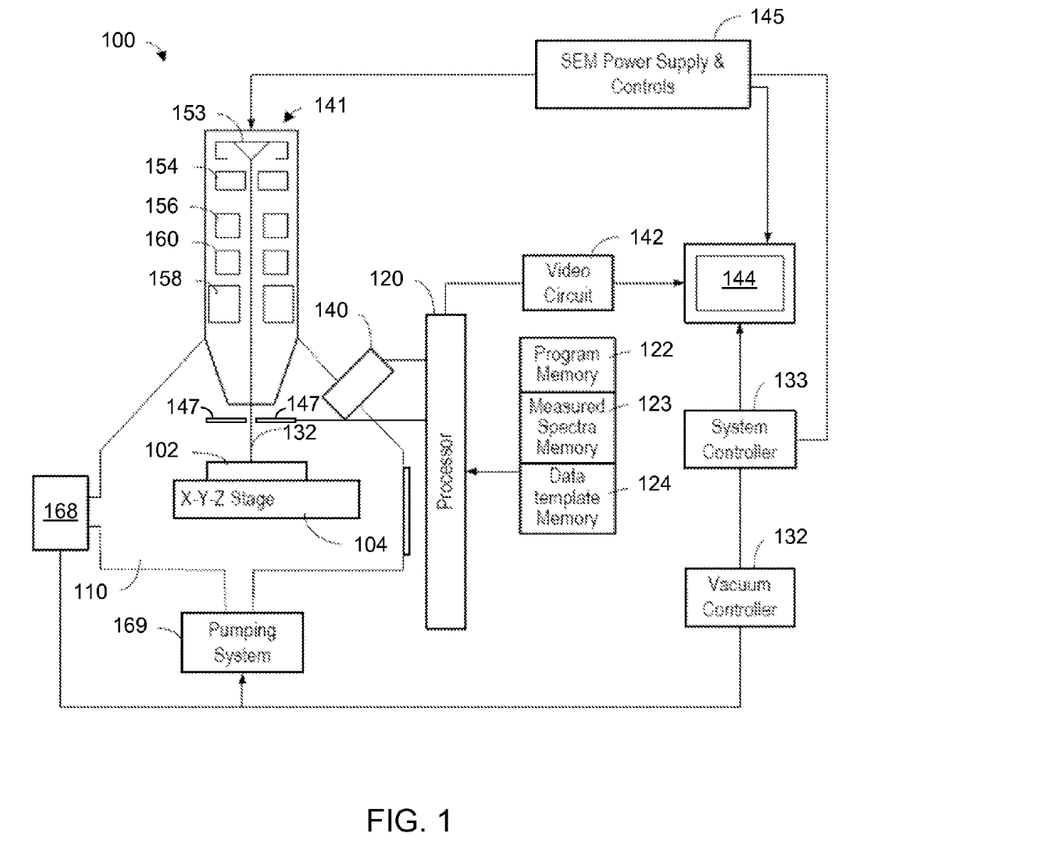
FIG. 1 is a scanning electron microscope suitable for implementing a mineral analysis system of the present invention.

FIG. 1 is an example of a scanning electron beam system 100 with an x-ray detector 140 suitable for analyzing samples prepared according to the present invention. A scanning electron microscope 141, along with power supply and control unit 145, is provided with system 100. An electron beam 132 is emitted from a cathode 153 by applying voltage between cathode 153 and an anode 154. Electron beam 132 is focused to a fine spot by means of a condensing lens 156 and an objective lens 158. Electron beam 132 is scanned two-dimensionally on the specimen by means of a deflection coil 160. Operation of condensing lens 156, objective lens 158, and deflection coil 160 is controlled by power supply and control unit 145.

A system controller 133 controls the operations of the various parts of scanning electron beam system 100. The vacuum chamber 110 is evacuated with ion pump 168 and mechanical pumping system 169 under the control of vacuum controller 132.

Electron beam 132 can be focused onto sample 102, which is on movable X-Y stage 104 within lower vacuum chamber 110. When the electrons in the electron beam strike sample 102, the sample gives off x-rays whose energy correlated to the elements in the sample. X-rays having energy inherent to the elemental composition of the sample are produced in the vicinity of the electron beam incident region. Emitted x-rays are collected by x-ray detector 140, preferably an energy dispersive detector of the silicon drift detector type, although other types of detectors could be employed, which generates a signal having an amplitude proportional to the energy of the detected x-ray. Backscattered electrons are detected by backscatter electron detector 147, which can comprise, for example, a microchannel plate or solid state detector.

Output from x-ray detector 140 is amplified and sorted by the processor 120, which counts and sorts the total number of X-rays detected during a specified period of time, at a selected energy and energy resolution, and a channel width (energy range) of preferably between 10-20 eV per channel. Similarly, output from BSE detector 147 is amplified and processed by processor 120. Processor 120 can comprise a computer processor; operator interface means (such as a keyboard or computer mouse); program memory 122 for storing data and executable instructions; interface means for data input and output; executable software instructions embodied in executable computer program code; and display 144 for displaying backscattered electron images and the results of a multivariate spectral analysis by way of video circuit 142.

Processor 120 can be a part of a standard laboratory personal computer, and is typically coupled to at least some form of computer-readable media. Computer-readable media, which include both volatile and nonvolatile media, removable and non-removable media, may be any available medium that can be accessed by processor 120. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 120.

Program memory 122 can include computer storage media in the form of removable and/or non-removable, volatile and/or nonvolatile memory and can provide storage of computer-readable instructions, data structures, program modules and other data. Generally, the processor 120 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained from the system can be stored in a portion of memory 122, such as the measured spectra memory portion 123. Data template memory portion 124 stores data templates, such as definitions of known spectra of elements or, in some embodiments, known diffraction patterns of materials.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

Figure 2:
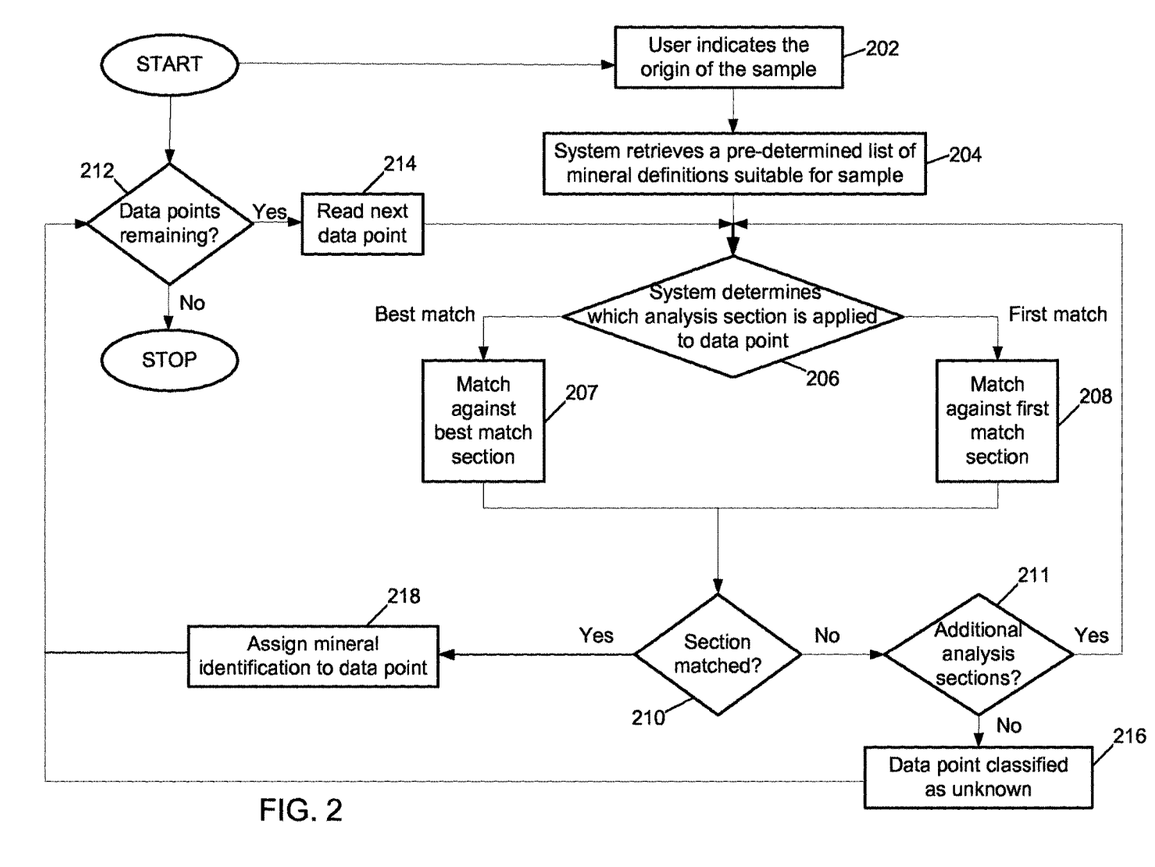
FIG. 2 is a flow chart of an embodiment of the invention.

FIG. 2 shows an overview of a preferred embodiment of a mineral analyzer in accordance with the invention. In step 202 a user of the system indicates the origin of the sample, such as being from a Copper-Lead-Zinc deposit. Knowing the origin reduces the number of minerals that are likely to be in sample, reducing the number of comparisons required and thereby reducing analysis time. In step 204, the system retrieves a pre-determined list of mineral definitions suitable for the sample. By "mineral definition" is meant an analysis protocol that when followed will determine the minerals present in the sample, thereby defining the minerals in terms of analysis rules. The list of mineral definitions is comprised of one or more analysis sections, where in one embodiment each analysis section is either a 'First Match' or 'Best Match' section. Once the user has indicated the origin, and the data points (x-ray spectrum and electron backscatter data) are obtained from the sample, the data points are analyzed to determine the mineral. Each data point can be analyzed immediately or multiple data points can be obtained and then analyzed.

In step 206, the system determines which analysis section is to be applied to the data point. In one embodiment, the first analysis section applied uses a rules-based, first match analysis in step 208. In decision step 210, if the analysis section has identified the mineral composition of the data point, then the data point is assigned its mineral identification in step 218. If it is determined in decision block 212 that there are additional data points to be analyzed, the next data point is read in step 214 and the analysis repeats the analysis from step 206.

If in step 210, the analysis section fails to identify the composition of the data point, the system determines in decision step 211 if additional analysis sections are available. If available, then the system selects a different analysis section in step 206. For example, if the data point did not meet the criteria for any mineral under the rules-based analysis, then a best match analysis is performed in step 207. If it is determined in step 210 that the best match analysis in step 207 determined the mineral composition of the data point, then the analysis of that data point is complete. If it is then determined in decision block 212 that there are additional data points, the next data point is read in step 214 and the analysis repeats the analysis from step 206. If it is determined in decision block 210 that the best match analysis section failed, and it is determined in decision block 211 that there is an additional analysis section remaining, then a different analysis section is selected in decision block 206. For example, the third analysis section may be a second, first match, rules-based analysis system in step 208, with different rules than the first analysis section. In another embodiment, the third analysis section may be another best match analysis section in section 207 using a different matching algorithm or a lower threshold. Again, if the mineral composition of the data point was found to be determined in block 210, then the data point is assigned its mineral identification in step 218. And if it is then determined in decision block 212 that there are additional data points to be analyzed, the next data point is read in step 214 and the analysis repeats the analysis from step 206. If the mineral composition of the data point is not identified, and it is determined in step 211 that there is an additional analysis section, then the process returns to step 206 to apply another analysis section. If no additional analysis sections are available, the data point may be classified as "unknown" in step 216. In one embodiment, the rules in the third analysis section are less stringent than the rules in the first analysis section or the matching threshold in the best match section, so the third analysis section is likely to find at least a general classification for the data point.

Figure 3:
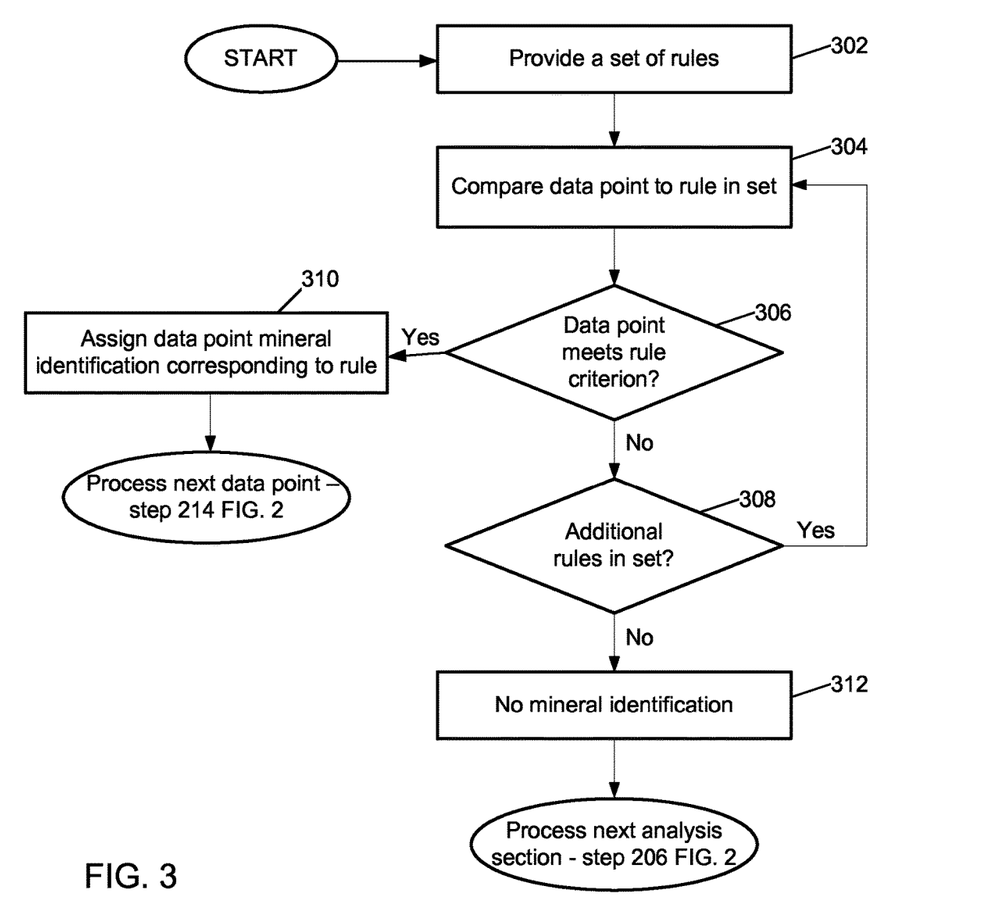
FIG. 3 is a flow chart of the first match algorithm portion of the embodiment of FIG. 2.

FIG. 3 shows a 'first match' analysis section in more detail. This analysis is similar to a QEMSCAN Species Identification Protocol (SIP) rule, described, for example, in U.S. Pat. Publication No. 2011/0144922 is a Method and System for Spectrum Data Analysis, which is assigned to the assignee of the present invention. A first match analysis section uses a number of entries in a rules table. Each rule consists of one or more criteria, such as the height of an x-ray peak at a specific energy range, or a backscatter electron intensity value, that must be met to classify the data point as a particular mineral. For example, one rule may state that if the BSE value is less than 30, the data point represents the resin used to embed the mineral sample, and so that data point may be discarded. Another rule may indicate that if the BSE value is less than 1000 counts per second, the electron beam is positioned at a crack in the sample, and the data point can be discarded. Another rule may state that if the composition of silicon is between 45% and 47% and oxygen is between 52% and 55%, then the mineral is quartz.

In step 302, a set of rules in a particular sequence is provided. In step 304, a data point is compared to the first rule in the set. If the data point meets the criteria, decision block 306 shows that the composition of the data point is considered to be the mineral corresponding to the rule and the identification process is complete. If in step 306, the analysis section fails to identify the composition of the data point, the system determines in decision step 308 if additional rules are available. If available, then the next rule is applied to the data point in step 304. The process continues until either the mineral is identified in step 310, or all rules have been applied, and the data point does not meet the criteria of any rule in step 312. If the mineral is identified, then the system continues to process the next data point in step 214 of FIG. 2. If not, then the system continues to process the next analysis section in step 206 of FIG. 2.

The process of FIG. 3 may be used to remove bad data points, or quickly identify areas that are definitely not of interest such as the resin used to mount the sample. The process of FIG. 3 may also be used as a final analysis section that classifies a mineral into a broad category, if it was not possible to specifically identify the mineral using more specific rules or matching.

The data point, that is, the unknown spectrum, is checked sequentially against each of the rules until either a match is found or all the rules have been checked. If the 'First Match' section provides a positive result, the result is taken as the mineral identification. If the 'First Match' section does not result in a match, then the process determines if the 'Best Match' section can be used.

Figure 4:
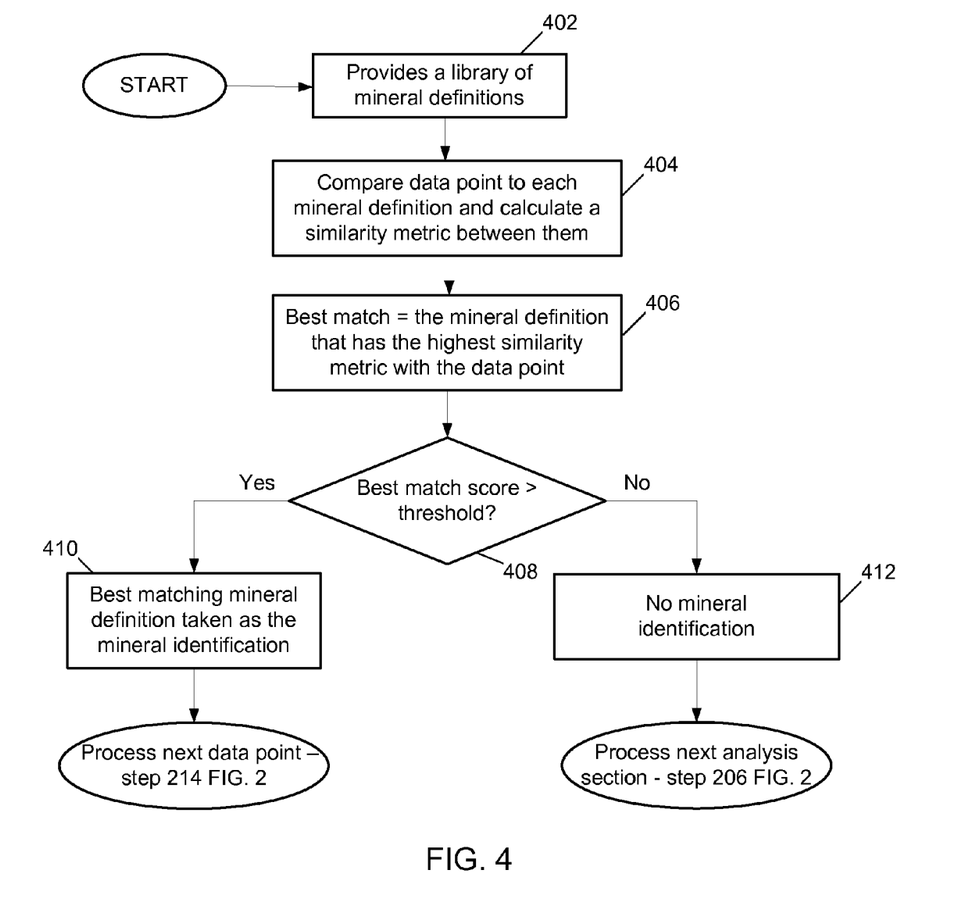
FIG. 4 is a flow chart of the best match algorithm portion of the embodiment of FIG. 2.

A "Best Match" analysis section consists of mineral definitions and a threshold value. A preferred similarity metric is described in "Mineral Identification Using Mineral Definitions Including Variability" as described in U.S. patent application Ser. No. 13/661,774. FIG. 4 shows that the steps of a "Best Match" analysis section. In step 402, a library of mineral definitions is provided. In step 404, the data point is compared to each of the mineral definitions in the library, and a similarity metric between the data point and each mineral definition in a library is calculated. When all minerals have been checked, in step 406, the mineral definition that has the highest similarity metric with the data point is taken as the best match. In step 408, the similarity metric of the best match is compared to a pre-specified threshold value, and, if the threshold is met, the best matching mineral definition is taken as the mineral identification in step 410. And the system continues to process the next data point in step 214 of FIG. 2. If the metric falls below the threshold, then no mineral identification is assigned in step 412 and, as described in step 206 of FIG. 2, another analysis section is applied. For example, the third section might be another "first match" section using different rules than the first "first match" section.

For example, the data point may be compared to Chalcopyrite, having a composition of Fe 30.43%, Cu 34.63%, S 34.94%, and having an average atomic number of 23.54, and to Galena, having a composition of S 13.40%, Pb 86.60% and having an average atomic number of 73.16%. If the data point fails to match Chalcopyrite or Galena with a match of, for example, 95%, then the data point is examined again using a second "first match" section having rules different from the original "first match" section. This second match section, being applied only after a match is not found, can be more generic. For example, a rule can state that if the Si composition is greater than 30%, the mineral is classified as "other silicates" and if the mineral has a composition of greater than 30% sulfur, the mineral is classified as "other sulphides."

While the embodiment above compares the data point with data from known minerals, other embodiments can first elements present, and then determine the minerals present from the identity and quantity of the elements present in the data point.

Further, whenever the terms "automatic," "automated," or similar terms are used herein, those terms will be understood to include manual initiation of the automatic or automated process or step. Whenever a scan or image is being processed automatically using computer processing, it should be understood that the raw image data can be processed without ever generating an actual viewable image. In the following discussion and in the claims, the terms "including" and "comprising" are used in an open-ended fashion, and thus should be interpreted to mean "including, but not limited to . . . ."

To the extent that any term is not specially defined in this specification, the intent is that the term is to be given its plain and ordinary meaning. The accompanying drawings are intended to aid in understanding the present invention and, unless otherwise indicated, are not drawn to scale. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for determining the mineral content of a sample, said method comprising:
    placing a sample in a scanning electron microscope;
    directing an electron beam to a point on the sample to obtain an x-ray spectrum of the sample and a backscatter electron intensity value, the x-ray spectrum and the backscatter electron intensity value corresponding to a data point, the data point having an associated mineral composition;
    sequentially applying rules from a first set of rules to the x-ray spectrum of the data point, wherein each rule identifies a mineral composition and comprises one or more criteria corresponding to the mineral composition that the rule identifies, and applying the rule comprises comparing the x-ray spectrum of the data point to the one or more criteria of the rule;
    identifying the mineral composition of the data point as the mineral composition of the first rule of the first set of rules applied to the x-ray spectrum of the data point in which the one or more criteria are satisfied;
    if and only if the x-ray spectrum of the data point fails to satisfy the one or more criteria of any of the rules of the first set of rules, comparing the x-ray spectrum of the data point to x-ray spectra of different mineral definitions in a library of mineral definitions to determine which of the minerals defined in the library is a best match for the data point; and
    if the value of a metric of similarity between the x-ray spectrum of the data point and the x-ray spectrum of the mineral definition for the best matching mineral in the library meets a predetermined threshold, identifying the mineral composition of the data point as the mineral composition corresponding to the best matching mineral defined in the library.

2. The method of claim 1, further comprising if the value of the metric of similarity between the x-ray spectrum of the data point and the x-ray spectrum of the best matching mineral defined in the library fails to meet the predetermined threshold:
    sequentially applying rules from a second set of rules to the data point, wherein each rule of the second set of rules identifies a mineral composition and comprises one or more criteria corresponding to the mineral composition that the rule identifies, and applying the rule comprises comparing the data point to the one or more criteria of the rule; and identifying the mineral composition of the data point as the mineral composition of the first rule of the second set of rules applied to the data point in which the one or more criteria are satisfied.

3. The method of claim 1, in which comparing the x-ray spectrum of the data point to x-ray spectra of different mineral definitions in a library of mineral definitions to determine which of the minerals defined in the library is a best match for the data point further comprises comparing the backscatter electron intensity value of the data point to backscatter electron intensity values corresponding to minerals defined in the library.

4. The method of claim 1, in which sequentially applying rules from a first set of rules to the x-ray spectrum of the data point identifies bad data points or identifies parts of the sample that do not need detailed analysis.

5. The method of claim 1, in which comparing the x-ray spectrum of the data point to x-ray spectra of different mineral definitions in a library of mineral definitions to determine which of the minerals defined in the library is a best match for the data point comprises calculating similarity metrics between the data point and each of the mineral definitions in the library of mineral definitions.

6. The method of claim 5 in which calculating similarity metrics includes determining probabilities that the library mineral will produce the values observed for the data point.

7. The method of claim 5 in which calculating similarity metrics includes calculating a chi squared value.

8. The method of claim 1, in which sequentially applying rules from a first set of rules to the x-ray spectrum of the data point includes comparing the data point to a criterion that includes the height of an x-ray peak at a specific energy range.

9. The method of claim 8, in which one of the criteria is a backscatter electron intensity value.

10. A scanning electron microscope system for determining the mineral content of a mineral sample, comprising:
an electron beam column for directing an electron beam toward a mineral sample;
a detector for measuring the energy or wavelength of x-rays emitted from the mineral sample in response to an impingement on the mineral sample of electrons in the electron beam to create an x-ray spectrum of a data point;
a processor for executing computer instructions to determine the minerals present in the mineral sample; and
a computer memory containing computer instructions configured for:
sequentially comparing the x-ray spectrum of the data point to criteria within a first set of rules, each criterion corresponding to a mineral composition, and identifying the mineral composition of the data point as the mineral composition corresponding to the first satisfied criterion;
if and only if the x-ray spectrum of the data point fails to satisfy any of the criteria in the first set of rules, comparing the x-ray spectrum of the data point to x-ray spectra of mineral definitions in a library of mineral definitions to determine which of the minerals defined in the library is a best match for the data point; and
if the match between the x-ray spectrum of the data point and the x-ray spectrum of the mineral definition for the best matching mineral in the library meets a predetermined threshold, identifying the mineral composition of the data point as the mineral composition corresponding to the best matching mineral defined in the library.

11. The scanning electron microscope system of claim 10, in which the computer instructions further comprise instructions for, if the match between the x-ray spectrum of the data point and the best matching mineral defined in the library fails to meet the predetermined threshold, sequentially comparing the data point to criteria within a second set of rules, each criterion corresponding to a mineral composition, and identifying the mineral composition of the data point as the mineral composition corresponding to the first satisfied criterion within the second set of rules.

12. The scanning electron microscope system of claim 10, in which the computer instructions for comparing the x-ray spectrum of the data point to x-ray spectra of different mineral definitions in a library of mineral definitions to determine which of the minerals defined in the library is a best match for the data point further comprise computer instructions for comparing a backscatter electron intensity value of the data point to backscatter electron intensity values corresponding to minerals defined in the library.

13. The scanning electron microscope system of claim 10, in which the computer instructions for sequentially comparing the x-ray spectrum of the data point to criteria within a first set of rules comprise computer instructions for identifying bad data points or identifying parts of the mineral sample that do not need detailed analysis.

14. The scanning electron microscope system of claim 10, in which the computer instructions for comparing the x-ray spectrum of the data point to x-ray spectra of different mineral definitions in a library of mineral definitions to determine which of the minerals defined in the library is a best match for the data point comprise computer instructions for calculating similarity metrics between the data point and each of the mineral definitions in the library of mineral definitions.

15. A scanning electron microscope system for determining the mineral content of a mineral sample, comprising:
an electron beam column for directing an electron beam toward a mineral sample;
a detector for measuring the energy or wavelength of x-rays emitted from the mineral sample in response to an impingement on the mineral sample of electrons in the electron beam to create an x-ray spectrum of a data point;
a processor for executing computer instructions to determine the minerals present in the mineral sample; and
a computer memory containing computer instructions configured for:
sequentially applying rules from a first set of rules to the x-ray spectrum of the data point, wherein each rule identifies a mineral composition and comprises one or more criteria corresponding to the mineral composition that the rule identifies, and applying the rule comprises comparing the x-ray spectrum of the data point to the one or more criteria of the rule;
identifying the mineral composition of the data point as the mineral composition of the first rule of the first set of rules applied to the x-ray spectrum of the data point in which the one or more criteria are satisfied;
if and only if the x-ray spectrum of the data point fails to satisfy the one or more criteria of any of the rules of the first set of rules, comparing the x-ray spectrum of the data point to x-ray spectra of different mineral definitions in a library of mineral definitions to determine which of the minerals defined in the library is a best match for the data point; and if the value of a metric of similarity between the x-ray spectrum of the data point and the x-ray spectrum of the mineral definition for the best matching mineral in the library meets a predetermined threshold, identifying the mineral composition of the data point as the mineral composition corresponding to the best matching mineral defined in the library.

16. The scanning electron microscope system of claim 15, in which the computer instructions further comprise instructions for:

if the value of the metric of similarity between the x-ray spectrum of the data point and x-ray spectrum of the best matching mineral defined in the library fails to meet the predetermined threshold, sequentially applying rules from a second set of rules to the data point, wherein each rule of the second set of rules identifies a mineral composition and comprises one or more criteria corresponding to the mineral composition that the rule identifies, and applying the rule comprises comparing the data point to the one or more criteria of the rule; and identifying the mineral composition of the data point as the mineral composition of the first rule of the second set of rules applied to the data point in which the one or more criteria are satisfied.

17. The scanning electron microscope system of claim 15, in which the computer instructions for comparing the x-ray spectrum of the data point to x-ray spectra of different mineral definitions in a library of mineral definitions to determine which of the minerals defined in the library is a best match for the data point further comprise computer instructions comparing a backscatter electron intensity value of the data point to backscatter electron intensity values corresponding to minerals defined in the library.

18. The scanning electron microscope system of claim 15, in which the computer instructions for sequentially applying rules from a first set of rules to the x-ray spectrum of the data point comprise computer instructions for identifying bad data points or identifying parts of the mineral sample that do not need detailed analysis.

19. The scanning electron microscope system of claim 15, in which the computer instructions for comparing the x-ray spectrum of the data point to x-ray spectra of different mineral definitions in a library of mineral definitions to determine which of the minerals defined in the library is a best match for the data point comprise computer instructions for calculating similarity metrics between the data point and each of the mineral definitions in the library of mineral definitions.

* * * * *